United States Patent [19]

Merger et al.

[11] 4,273,934

[45] Jun. 16, 1981

[54] PREPARATION OF 3-HYDROXY-2,2,4-TRIMETHYLPENTYL ISOBUTYRATE

[75] Inventors: Franz Merger, Frankenthal; Hans-Juergen Foerster, Bobenheim-Roxheim, both of Fed. Rep. of Germany

[73] Assignee: BASF Aktiengesellschaft, Fed. Rep. of Germany

[21] Appl. No.: 31,013

[22] Filed: Apr. 17, 1979

[30] Foreign Application Priority Data

May 11, 1978 [DE] Fed. Rep. of Germany ....... 2820518

[51] Int. Cl.$^3$ .................... C07C 67/00; C07C 69/28
[52] U.S. Cl. .................. 560/238; 260/340.7; 568/463; 568/858; 560/240
[58] Field of Search ............... 560/238, 240; 260/340.7

[56] References Cited

U.S. PATENT DOCUMENTS

| 3,291,821 | 12/1966 | Perry et al. | 560/238 |
|---|---|---|---|
| 3,703,541 | 11/1972 | Takasu et al. | 560/238 |
| 3,718,689 | 2/1973 | McCain et al. | 560/238 |
| 4,017,537 | 4/1977 | McCollum et al. | 560/238 |

FOREIGN PATENT DOCUMENTS

| 646482 | 6/1937 | Fed. Rep. of Germany | 560/238 |
|---|---|---|---|
| 1291041 | 11/1969 | Fed. Rep. of Germany | 560/238 |

OTHER PUBLICATIONS

Monatsh. Chemie, 25, pp. 188-196, 1904.

*Primary Examiner*—Vivian Garner
*Attorney, Agent, or Firm*—Keil & Witherspoon

[57] ABSTRACT

3-Hydroxy-2,2,4-trimethylpentyl isobutyrate is prepared by reaction of isobutyraldehyde in the presence of an alkaline earth metal hydroxide and of carboxylic acids or the corresponding salts, under specific conditions in respect of reaction time and proportion and concentration of the hydroxide suspension. The product is a starting material for the preparation of dyes, pesticides, adhesives and surface coatings.

8 Claims, No Drawings

PREPARATION OF 3-HYDROXY-2,2,4-TRIMETHYLPENTYL ISOBUTYRATE

The present invention relates to a novel process for the preparation of 3-hydroxy-2,2,4-trimethylpentyl isobutyrate by reaction of isobutyraldehyde in the presence of an alkaline earth metal hydroxide and of carboxylic acids or the corresponding salts, under specific conditions in respect of reaction time and proportion and concentration of the hydroxide suspension.

Monatsh. Chemie, 25, 188–196, discloses the conversion of isobutyraldehyde to 3-hydroxy-2,2,4-trimethylpentyl isobutyrate in the presence of a calcium hydroxide suspension. However, the yields are very poor and a series of undesirable by-products such as isobutyraldol, isobutyraldoxane, 2,2,4-trimethylpentane-1,3-diol (resulting from hydrolysis) and isobutyl isobutyrate is formed.

German Pat. No. 646,482 describes the preparation of 1,3-glycol half-esters by condensing corresponding aldehydes, having only one hydrogen in the α-position to the carbonyl group, e.g., 2-methylpropanal, 2-methylbutanal or 2-methylpentanal, with solid sodium hydroxide or sodium amide as the catalyst, in the absence of a solvent. The process of working up by acidification with hydrochloric acid, washing neutral with water and subsequent steam distillation and distillation is relatively expensive. As already recorded in U.S. Pat. No. 3,718,689 (column 1, lines 10–22) the disadvantages related to the use of solid alkali in chemical processes are self-evident (difficulty of metering and dissolving the catalyst, and poor control of the operation); furthermore, solid NaOH deliquesces in air and constitutes a hazard to the personnel using this chemical. Regarding the prior art, German Pat. No. 646,482 expressly states (page 1, lines 27 to 31 and 58 to 60) that sodium acetate and aqueous calcium hydroxide suspension are unsuitable catalysts for the preparation of 3-hydroxy-2,2,4-trimethylpentyl isobutyrate, since they give very poor yields of end product and since the above by-products are formed.

U.S. Pat. No. 3,291,821 and U.S. Pat. No. 3,718,689 describe continuous processes using aqueous sodium hydroxide solution as the catalyst, in the former case using sodium hydroxide solution of from 5 to 20 percent strength by weight, and in the latter case of from 30 to 50 percent strength by weight. The yield in both processes is in general unsatisfactory and in the case of the process of U.S. Pat. No. 3,718,689 it fluctuates substantially during operation. It is true that both U.S. patents state that alkaline earth metal hydroxides can also be used as the catalysts, but in the Examples only alkali metal hydroxide solutions are used. At the same time, U.S. Pat. No. 3,718,689 claims, and shows in more detail, that the aqueous solutions of the hydroxides must have a concentration of at least 30 percent by weight of hydroxide, based on the total weight of the aqueous solution. This conditions shows that the process can virtually only be carried out with an alkali metal hydroxide solution, since an alkaline earth metal hydroxide could, at a concentration of at least 30 percent by weight, only be in the form of an aqueous suspension and not of an aqueous solution. An acid is not added to the starting mixture. As shown by U.S. Pat. No. 3,718,689, column 3, lines 10–15, the acid content of the aldehyde starting material should not exceed 0.5 percent by weight, based on the aldehyde; in the Examples, the proportion of acid is 0.36 percent by weight. U.S. Pat. No. 3,718,689 points out (column 4, lines 21–31) that to achieve optimum space-time yields the residence time should be at least 10 minutes and that the reaction mixture is advantageously worked up by carrying out a steam distillation at 125° C. and 2 atmospheres pressure, in order to cleave the isobutyraldoxane (trimer) obtained as a by-product and isolate the resulting aldehyde (monomer) as an azeotropic mixture with water. U.S. Pat. No. 3,291,821 recommends a similar azeotropic method of isolation.

U.S. Pat. No. 3,703,541 describes a process which gives a conversion of 84.3 percent, and a yield of 3-hydroxy-2,2,4-trimethylpentyl isobutyrate of 92 percent; however, the type of catalysis, using alkali metal phenolates in, for example, toluene as the solvent, is involved, not free from problems and expensive. Furthermore, the patent points out that an increase in the water content decreases the conversion and the selectivity, and hence the water content must be less than 5,500 ppm. In the Examples, the water content is in most cases about 1,000 ppm. The industrial dehydration of isobutyraldehyde which the process thus requires is expensive.

We have found that 3-hydroxy-2,2,4-trimethylpentyl isobutyrate is obtained in an advantageous manner by reaction of isobutyraldehyde in the presence of basic compounds and of water, if the isobutyraldehyde is reacted in the presence of from 1.5 to 5 percent by weight, based on isobutyraldehyde, of a carboxylic acid in the form of the free acid, or an alkali metal salt and/or alkaline earth metal salt thereof, and in the presence of from 0.01 to 0.1 mole of alkaline earth metal hydroxide and from 0.04 to 1 mole of water per mole of isobutyraldehyde, for a reaction time of from 10 to 300 minutes.

The reaction can be represented by the following equation:

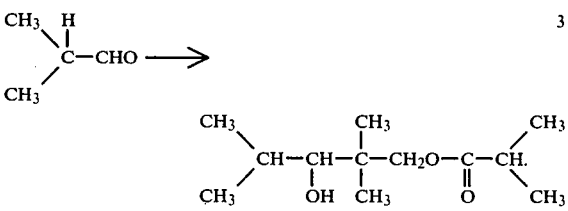

The process according to the invention is based on the observation that only a very specific combination of selected characteristics, which have never previously been recognized as being advantageous when used in the combination according to the invention, permits the achievement of optimum results. Compared to the conventional processes, the process of the invention gives 3-hydroxy-2,2,4-trimethylpentyl isobutyrate more simply and more economically, in better yield and greater purity. Far less isobutyraldol and isobutyraldoxane are produced. Furthermore, the catalysts claimed exert substantially less catalysis on the secondary reactions of 3-hydroxy-2,2,4-trimethylpentyl isobutyrate to give 2,2,4-trimethylpentane-1,3-diol and the diisobutyrate of the latter.

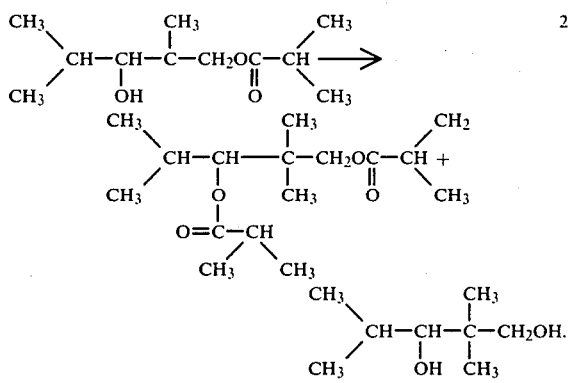

High yields of end product are obtained in an easily isolated form. A substantial advantage is that water can be used according to the invention, since isobutyraldehyde containing water is industrially more easily obtainable than anhydrous isobutyraldehyde. The careful exclusion of oxygen is not necessary; it is even possible to produce the acid in situ by passing oxygen-containing gases into or over the reaction mixture. In the presence of the carboxylic acids according to the invention, or of their salts, the reaction takes place substantially more rapidly than in the presence of the alkaline earth metal hydroxide alone, and takes place more selectively and with higher conversion than in the conventional processes. Expensive working-up steps, for example steam distillation, are not necessary. All these advantageous results are surprising in view of the prior art.

The isobutyraldehyde can as a rule contain water up to the limit of solubility thereof, but preferably contains from 0 to 5 percent by weight of water, based on isobutyraldehyde. This water content is included in the concentration of water present in the total reaction mixture according to the invention. The reaction is in general carried out at from 20° to 150° C., preferably from 40° to 90° C., under atmospheric or superatmospheric pressure, e.g., at from 0.98 to 10 bar, continuously or batchwise. Preferably, barium hydroxide, strontium hydroxide and/or, in particular, calcium hydroxide is used as the alkaline earth metal hydroxide, advantageously in an amount of from 0.01 to 0.1, preferably from 0.015 to 0.07, mole per mole of isobutyraldehyde. During the reaction, the alkaline earth metal hydroxide is not in aqueous solution but in general in aqueous suspension or, occasionally, in the form of a moist reaction mass. The concentration of water in the reaction mixture is from 0.04 to 1, preferably from 0.08 to 0.5, especially from 0.16 to 0.3, mole per mole of isobutyraldehyde. In general, no solvent other than water is used. The reaction time is from 10 to 300, preferably from 20 to 200, especially from 30 to 180, minutes.

Carboxylic acids which may be used are polycarboxylic, advantageously dicarboxylic, but preferably monocarboxylic; acids of at least 3 carbon atoms are particularly preferred. The acids are advantageously used in the form of their magnesium salts, lithium salts or potassium salts or especially barium salts or strontium salts or preferably calcium salts or sodium salts, or as the free acids. From 1.5 to 5, advantageously from 1.5 to 3, preferably from 1.5 to 2, percent by weight of carboxylic acid, based on isobutyraldehyde, is added, either in the form of the free acid or of an alkali metal salt or alkaline earth metal salt or of a mixture of the acid and an alkali metal salt thereof or as a mixture of the acid and an alkaline earth metal salt thereof or as a mixture of an alkali metal salt and an alkaline earth metal salt of a carboxylic acid or as a mixture of the carboxylic acid, an alkali metal salt thereof and an alkaline earth metal salt thereof. The above percentages by weight are calculated as free 100 percent strength carboxylic acid, without taking account of the carboxylic acid compound actually used. Mixtures of several carboxylic acids, alkali metal salts of carboxylic acids and/or alkaline earth metal salts of carboxylic acids may also be used, as may polybasic carboxylic acids which have only partially been neutralized with an alkali metal base and/or alkaline earth metal base.

Examples of suitable acids are aliphatic carboxylic acids, especially alkanecarboxylic acids of 3 to 10 carbon atoms, e.g., propionic acid, butyric acid, isobutyric acid, caproic acid, pelargonic acid, $\beta$-isobutyroxypivalic acid, $\alpha$-methylpentanoic acid, 3,5,5-trimethylhexanoic acid, 2,2,4-trimethyl-3-hydroxy-pentanoic acid, 2-ethylpent-2-en-1-oic acid, 2-ethylhexanecarboxylic acid, $\alpha$-ethylbutyric acid, isovaleric acid and valeric acid; cycloaliphatic carboxylic acids, especially cycloalkylcarboxylic acids of 6 to 8 carbon atoms, araliphatic carboxylic acids, especially of 8 to 12 carbon atoms, and aromatic carboxylic acids, especially of 7 to 12 carbon atoms, e.g., benzoic acid, phenylpropionic acid, phenylacetic acid and mixtures thereof; the corresponding sodium or calcium salts may also be used. Preferred acids are isobutyric acid, 2,2,4-trimethyl-3-hydroxy-pentanoic acid, 2-ethylhexanecarboxylic acid, benzoic acid, phenylpropionic acid and $\alpha$-methylpentanecarboxylic acid.

The reaction may be carried out as follows: a mixture of isobutyraldehyde, alkaline earth metal hydroxide, water and carboxylic acid is kept at the reaction temperature for the reaction time. For example, the desired amount of water and acid can be added to the isobutyraldehyde and the catalyst can then be suspended in the mixture. The end product is subsequently isolated from the reaction mixture in the conventional manner, for example by neutralizing and distilling the mixture.

3-Hydroxy-2,2,4-trimethylpentyl isobutyrate, prepared by the process of the invention, is a valuable starting material for the preparation of dyes, pesticides, adhesives and surface coatings. It is an excellent flow control agent for adhesives and surface coatings based on polyvinyl acetate and polyacrylate. It can also be used as a solvent and plasticizer in latex emulsions. it esters are used to plasticize polymers. Regarding its use, reference may be made to the above publications and to German Pat. No. 1,291,041.

In the Examples which follow, parts are by weight.

EXAMPLE 1

900 parts of isobutyraldehyde, 54 parts of Ca(OH)$_2$, 54 parts of water and 18 parts of isobutyric acid are refluxed for 2 hours at 60°-80° C. under nitrogen. The product contains, according to gas chromatographic analysis, 711.9 parts of 3-hydroxy-2,2,4-trimethylpentyl isobutyrate (79.1% of theory), 11.7 parts of 2,2,4-trimethylpentane-1,3-diol and 166.5 parts of unconverted starting material. The reaction mixture is then neutralized with 34 parts of carbon dioxide and the end product is isolated by distillation. 3-Hydroxy-2,2,4-trimethylpentyl isobutyrate has a boiling point of 128° C./20 mbar.

EXAMPLE 2

250 parts of isobutyraldehyde, 15 parts of Ca(OH)$_2$, 15 parts of water and 5 parts of isobutyric acid are refluxed for 2 hours at 60°–80° C. in the presence of air. The product contains, according to gas chromatographic analysis, 188.8 parts of 3-hydroxy-2,2,4-trimethylpentyl isobutyrate (75.5% of theory), 4.4 parts of 2,2,4-trimethylpentane-1,3-diol and 52.8 parts of unconverted starting material. The reaction mixture is then neutralized with 10 parts of carbon dioxide and the end product is isolated by distillation. 3-Hydroxy-2,2,4-trimethylpentyl isobutyrate has a boiling point of 128° C./20 mbar.

EXAMPLE 3

250 parts of isobutyraldehyde, 15 parts of Ca(OH)$_2$, 15 parts of water and 5 parts of calcium isobutyrate are refluxed for 2 hours at 60°–74° C. in the presence of air. The product contains, according to gas chromatographic analysis, 153.3 parts of 3-hydroxy-2,2,4-trimethylpentyl isobutyrate (61.3% of theory), 0.7 part of 2,2,4-trimethylpentane-1,3-diol and 92.5 parts of unconverted starting material. The reaction mixture is then neutralized with 10 parts of carbon dioxide and the end product is isolated by distillation. 3-Hydroxy-2,2,4-trimethylpentyl isobutyrate has a boiling point of 128° C./20 mbar.

EXAMPLE 4

250 parts of isobutyraldehyde, 5 parts of Ca(OH)$_2$, 15 parts of water and 5 parts of isobutyric acid are refluxed for 3 hours at 60°–80° C. in the presence of air. The product contains, according to gas chromatographic analysis, 191.3 parts of 3-hydroxy-2,2,4-trimethylpentyl isobutyrate (76.5% of theory), 4 parts of 2,2,4-trimethylpentane-1,3-diol and 51 parts of unconverted starting material. The reaction mixture is then neutralized with 10 parts of carbon dioxide and the end product is isolated by distillation. 3-Hydroxy-2,2,4-trimethylpentyl isobutyrate has a boiling point of 128° C./20 mbar.

EXAMPLE 5

250 parts of isobutyraldehyde, 15 parts of Ca(OH)$_2$, 15 parts of water and 8.2 parts of 2-ethylhexanoic acid are refluxed for 2 hours at 60°–81° C. in the presence of air. The product contains, according to gas chromatographic analysis, 189.5 parts of 3-hydroxy-2,2,4-trimethylpentyl isobutyrate (75.8% of theory), 8.8 parts of 2,2,4-trimethylpentane-1,3-diol and 42.5 parts of unconverted starting material. The reaction mixture is then neutralized with 10 parts of carbon dioxide and the end product is isolated by distillation. 3-Hydroxy-2,2,4-trimethylpentyl isobutyrate has a boiling point of 128° C./20 mbar.

EXAMPLE 6

250 parts of isobutyraldehyde, 15 parts of Ca(OH)$_2$, 15 parts of water and 8.75 parts of 2,2,4-trimethyl-3-hydroxypentanoic acid are refluxed for 1.75 hours at 60°–80° C. in the presence of air. The product contains, according to gas chromatographic analysis, 191.5 parts of 3-hydroxy-2,2,4-trimethylpentyl isobutyrate (76.6% of theory), 9 parts of 2,2,4-trimethylpentane-1,3-diol and 37.8 parts of unconverted starting material. The reaction mixture is then neutralized with 10 parts of carbon dioxide and the end product is isolated by distillation. 3-Hydroxy-2,2,4-trimethylpentyl isobutyrate has a boiling point of 128° C./20 mbar.

EXAMPLE 7

250 parts of isobutyraldehyde, 15 parts of Ca(OH)$_2$, 15 parts of water and 5 parts of sodium benzoate are refluxed for 4 hours at 60°–80° C. in the presence of air. The product contains, according to gas chromatographic analysis, 200 parts of 3-hydroxy-2,2,4-trimethylpentyl isobutyrate (80% of theory), 10.3 parts of 2,2,4-trimethylpentane-1,3-diol and 32.5 parts of unconverted starting material. The reaction mixture is then neutralized with 10 parts of carbon dioxide and the end product is isolated by distillation. 3-Hydroxy-2,2,4-trimethylpentyl isobutyrate has a boiling point of 128° C./20 mbar.

EXAMPLE 8

250 parts of isobutyraldehyde, 15 parts of Ca(OH)$_2$, 15 parts of water and 5 parts of 2-phenylpropionic acid are refluxed for 2 hours at 60°–77° C. in the presence of air. The product contains, according to gas chromatographic analysis, 175.5 parts of 3-hydroxy-2,2,4-trimethylpentyl isobutyrate (70.2% of theory), 6.8 parts of 2,2,4-trimethylpentane-1,3-diol and 63.8 parts of unconverted starting material. The reaction mixture is then neutralized with 10 parts of carbon dioxide and the end product is isolated by distillation. 3-Hydroxy-2,2,4-trimethylpentyl isobutyrate has a boiling point of 128° C./20 mbar.

EXAMPLE 9

150 parts of isobutyraldehyde, 9 parts of Ba(OH)$_2$, 9 parts of water and 3 parts of isobutyric acid are refluxed for 0.25 hour at 60°–80° C. in the presence of air. The product contains, according to gas chromatographic analysis, 107.3 parts of 3-hydroxy-2,2,4-trimethylpentyl isobutyrate (71.5% of theory), 8.7 parts of 2,2,4-trimethylpentane-1,3-diol and 30.6 parts of unconverted starting material. The reaction mixture is then neutralized with 6 parts of carbon dioxide and the end product is isolated by distillation. 3-Hydroxy-2,2,4-trimethylpentyl isobutyrate has a boiling point of 128° C./20 mbar.

COMPARATIVE EXAMPLE

The reaction is carried out as described in Example 1, but without addition of isobutyric acid. The product contains, according to gas chromatographic analysis, 241.2 parts of 3-hydroxy-2,2,4-trimethylpentyl isobutyrate (26.8% of theory), 5 parts of 2,2,4-trimethylpentane-1,3-diol and 648 parts of unconverted starting material. The reaction mixture is then neutralized with 34 parts of carbon dioxide and the end product is isolated by distillation. 3-Hydroxy-2,2,4-trimethylpentyl isobutyrate has a boiling point of 128° C./20 mbar.

We claim:

1. A process for the preparation of 3-hydroxy-2,2,4-trimethylpentyl isobutyrate by reacting isobutyraldehyde in the presence of a basic compound and water, wherein isobutyraldehyde is reacted in the presence of from 1.5 to 5 percent by weight, based on isobutyraldehyde, of a carboxylic acid selected from the group consisting of isobutyric acid, 2,2,4-trimethyl-3-hydroxypentanoic acid, 2-ethylhexanecarboxylic acid, benzoic acid, phenylpropionic acid and α-methylpentanecarboxylic acid in the form of the free acid, or an alkali metal salt and/or alkaline earth metal salt thereof, and in the presence of from 0.01 to 0.1 mole of an alkaline earth metal hydroxide selected from the group consisting of barium hydroxide, strontium hydroxide and calcium hydroxide and from 0.04 to 1 mole of water per mole of isobutyraldehyde, for a reaction time of from 10 to 300 minutes.

2. A process as claimed in claim 1, wherein the reaction is carried out at from 0.98 to 10 bar.

3. A process as claimed in claim 1, wherein the reaction is carried out at from 20° to 150° C.

4. A process as claimed in claim 1, wherein the reaction is carried out at from 40° to 90° C.

5. A process as claimed in claim 1, wherein the reaction is carried out with from 0.015 to 0.07 mole of alkaline earth metal hydroxide per mole of isobutyraldehyde.

6. A process as claimed in claim 1, wherein the reaction is carried out with from 0.08 to 0.5 mole of water per mole of isobutyraldehyde.

7. A process as claimed in claim 1, wherein the reaction is carried out for a reaction time of from 20 to 200 minutes.

8. A process as claimed in claim 1, wherein the reaction is carried out with from 1.5 to 3 percent by weight of carboxylic acid, based on isobutyraldehyde.

* * * * *